United States Patent [19] [11] 4,396,608
Tenold [45] Aug. 2, 1983

[54] INTRAVENOUSLY INJECTABLE IMMUNE SERUM GLOBULIN

[75] Inventor: Robert A. Tenold, Benicia, Calif.

[73] Assignee: Cutter Laboratories, Berkeley, Calif.

[21] Appl. No.: 295,916

[22] Filed: Aug. 24, 1981

[51] Int. Cl.³ .............................................. C08L 89/00
[52] U.S. Cl. ..................................... 424/177; 424/85; 424/101; 260/112 B
[58] Field of Search ..................... 424/85, 101, 86, 87, 424/177; 260/112 B

[56] References Cited

U.S. PATENT DOCUMENTS 4,093,606 6/1978 Coval .............................. 260/112 B
4,186,192 1/1980 Lundblad ............................ 424/85

FOREIGN PATENT DOCUMENTS 47-37529 9/1972 Japan .

Primary Examiner—John C. Bleutge
Assistant Examiner—Patricia Short
Attorney, Agent, or Firm—Theodore J. Leitereg

[57] ABSTRACT

A composition is disclosed which comprises a solution in a pharmaceutically acceptable carrier of an immune serum globulin, said solution having an ionic strength and a pH to maintain the monomer content and the actual and latent anticomplement activity of the immune serum globulin such that the composition is intravenously injectable. Novel methods are disclosed for preparing the above composition.

14 Claims, No Drawings

INTRAVENOUSLY INJECTABLE IMMUNE SERUM GLOBULIN

BACKGROUND OF THE INVENTION

FIELD OF THE INVENTION

This invention relates to pharmaceutical compositions comprising novel intravenously injectable immune serum globulin, to a process for its production and to its use to administer immune serum globulin intravenously for human therapy.

Intramuscularly injectable gamma globulin preparations are known. One such product is "HYPER-TET" (Cutter Laboratories, Inc., Berkeley, Calif.).

The usual intramuscular gamma globulin preparations cannot safely be administered intravenously because such administration causes an unacceptably high incidence of reactions, especially in agammaglobulinemic recipients. These reactions have been associated with a decrease in serum complement levels, apparently caused by complement binding by the administered gamma globulin. S. Barandun et al., *Vox Sang.* 7, 157-174 (1962). The ability of gamma globulin to bind complement, termed anticomplementary, is greatly increased as a result of denaturation brought about during the fractionation procedure, in particular by aggregation to high molecular weight species. The complement binding mechanism of these aggregates appears to be identical to that of antigen-antibody complexes. D. M. Marcus, *J. Immunol.* 84, 273-284 (1960). When the aggregates are removed by ultracentrifugation at 100,000 x gravity, a product low in anticomplement activity is obtained which is well tolerated upon intravenous injection. Barandun et al., supra.

Several approaches have been taken to the problem of rendering gamma globulin safe for intravenous administration. All of these are dependent on eliminating its anticomplement activity. Ultracentrifugation (cited above) is technically unfeasible, and the product so derived regains its anticomplement activity upon storage. Treatment of gamma globulin with the enzyme pepsin at pH 4.0 results in proteolytic cleavage of the molecule to give a fragment of about 10,000 molecular weight which has a sedimentation coefficient in the ultracentrifuge of about 5S,A. Nisonoff et al., *Science*, 132, 1770-1771 (1960). Even though this surviving fragment retains bivalent antibody activity and lacks anticomplement activity and is well tolerated and efficacious in intravenous administration, W. Baumgarten, *Vox Sang.* 13, 84 (1967), the therapeutic effect provided is of unacceptably short duration since it is rapidly excreted, having a circulating half-life of only 18 hours, perhaps somewhat longer in agammaglobulinemic patients, compared to 19.8 days for unmodified gamma globulin. E. Merler et al., *Vox Sang.* 13, 102 (1967); B. Jager, *Arch. Intern. Med.* 119, 60 (1967). Although the much reduced half-life of pepsin treated gamma globulin is probably due in part to the drastic reduction in size of the molecule, there are indications that the rate of catabolism of gamma globulin is related to specific properties of the portion of the molecule digested by pepsin. J. L. Fahey et al., *J. Exper. Med.*, 118, 1845-1868 (1963). This portion of the molecule remains intact in the present invention. An additional disadvantage of the pepsin treatment procedure is that the pepsin which remains present is of animal origin and can stimulate antibody production, particularly upon repeated administration. C. Blatrix et al., *Presse Med.* 77, 635-637 (1969). The use of plasmin of human origin avoids this difficulty and is the basis of a different process for preparation of intravenous gamma globulin.

Treatment of gamma globulin with human plasmin results in cleavage into three components of about 50,000 molecular weight. J. T. Sgouris, *Vox Sang.* 13, 71 (1967). When sufficiently low levels of plasmin are used, only about 15 percent of the molecules are cleaved, with 85 percent remaining as intact gamma globulin. Sgouris, supra. The intact gamma globulin remaining undigested shows little anticomplement activity and has been administered intravenously without adverse reactions. J. Hinman et al., *Vox Sang.* 13, 85 (1967). The material thus prepared appears to retain in vitro and in vivo protective activity. F. K. Fitzpatrick, *Vox Sang*, 13, 85 (1967). One disadvantage of this approach is that the plasmin cannot be completely removed. Thus, degradation continues even when the material is stored at 4° C.

Incubation of gamma globulin at pH 4.0 at 37° C. for various lengths of time has been observed to reduce the anticomplement activity to low levels. It has been suggested that this result may arise from a small quantity of serum enzyme present as an impurity in the gamma globulin. Blatrix et al., supra. As with the plasmin treated gamma globulin, this "pH 4.0 gamma globulin" has been found to regain anticomplement activity, upon storage, at an unpredictable rate, so that it is necessary to assay anticomplement activity before administration to a patient. J. Malgras et al., *Rev. Franc. Trans.*, 13, 173 (1970).

Both plasmin treated gamma globulin, Hinman et al., supra, and pH 4.0 gamma globulin, H. Koblet et al., *Vox Sang.* 13, 93 (1967); J. V. Wells et al., *Austr. Ann. Med.* 18, 271 (1969); Barandun et al., *Monogr. Allergy*, Vol. 9, 39-60 (1975), Barandun et al., *Vox Sang.*, Vol. 7, 157-174 (1962), have shorter half-lives in vivo than unmodified gamma globulin. For example, the half-life in normal patients of pH 4.0 gamma globulin is about 14 days, Koblet et al., supra, while the plasmin treated material shows a half-life of 16 days, Merler et al., supra.

The Centre National de Transfusion Sanguine (C.N.T.S.) in Paris has, by careful fractionation and filtration of gamma globulin from selected fresh plasma, produced an intravenously injectable gamma globulin with low anticomplement activity. Blatrix et al., supra; ibid., *Presse Med.*, 77, 159-161 (1969); M. Steinbuch et al., *Vox Sang.* 13, 103 (1967). It is apparently not totally devoid of anticomplement activity, as it must be administered carefully and reactions do occur in some patients. Cortisone may be given prior to injection to eliminate these reactions, but the apparent incomplete removal of anticomplement activity would seem to be detrimental to its widespread use.

The effects on anticomplement activity of reduction of disulfide linkages of gamma globulin followed by reaction with a blocking agent has been investigated in the prior art. S. Barandun et al., supra, found that treatment of a 7 percent solution of gamma globulin with 0.2 M cysteamine, followed by 0.2 M iodoacetamide, resulted in almost complete loss of anticomplement activity whereas treatment with cysteamine or iodoacetamide alone did not significantly decrease anticomplement activity. Because of the toxicity of iodoacetamide, these investigators did not pursue this approach to an intravenously injectable gamma globulin.

A modified immune serum globulin was described in U.S. Pat. No. 3,903,262. The immune serum globulin was rendered intravenously injectable by first reducing to —SH groups a portion of the disulfide linkages of the molecule and then alkylating the —SH groups. After the product was separated from the reaction mixture, it was sterilized. The so-produced material was intravenously injectable, substantially free from both actual and latent anticomplement activity, having substantially the biological half-life and spectrum of antibody activity of corresponding unmodified immune serum globulin.

Currently, there are several intravenously injectable gamma globulin products available outside the United States. One such product is INTRAGLOBIN of Biotest in Frankfurt. This product is made by beta-propriolactone treatment of gamma globulin (Stephan, *Vox. Sang.*, 1975, Vol. 28, pp. 422-437). The material has a molar concentration of sodium ion of about 0.18 and of chloride of about 0.27. The beta-propiolactone used in its preparation is suspected as a carcinogen.

Another intravenously injectable product is manufactured by Green Cross Corporation of Japan (U.S. Pat. No. 4,168,303). It is a lyophilized, natural gamma globulin preparation having an anticomplementary activity of less than or equal to 20 C'H50 units and 0.06-0.26 parts by weight of a neutral mineral salt such as sodium chloride.

The Swiss Red Cross has an immunoglobulin SCR for intravenous administration. SCR contains more than 80% of monomeric IgG and minor fractions of dimeric, polymeric, and fragmented IgG as well as traces of IgA and IgM. The distribution of IgG subclasses equals that of normal serum. The product is manufactured in lyophilized form and contains 3 g of protein, 5 g of saccharose and a small quantity of sodium chloride per unit. A diluent (100 ml) contains 0.9% sodium chloride.

VENOGLOBULIN (Green Cross Corporation of Japan) is prepared by treating gamma globulin with plasmin. It also contains 0.5 parts of a protein stabilizer (e.g. amino acetate) per 1 part by weight of plasmin treated gamma globulin. The product is distributed as a white powder and is dissolved in a diluent for use. The resulting solution is clear or slightly turbid and has a pH of 6.4-7.4.

An intravenously injectable gamma globulin has been developed by Schwab of Germany and contains 50 mg per ml immunoglobulin, 7 mg/ml glycin, and 7 mg/ml sodium chloride.

Schura of Germany manufactures an intravenously injectable gamma globulin by adsorption onto hydroxyethyl starch. The product is distributed as a solution having a pH of 6.7 and a conductivity of 450 mosm. and containing 2.5% glucose, 165 meq/l of sodium ion and 120 meq/l of chloride ion.

VEINOGLOBULINE is available from Institute Merieux of France. It is a plasmin-treated gamma globulin distributed as a lyophilized powder containing 5 g. of protein and enough glycine and sodium chloride to insure pH and stability. The diluent is 100 ml of water for injection containing 0.9 g. of sodium chloride or isotonic glucose.

U.S. Pat. No. 4,160,763, assigned to Behringwerke AG of Germany, is directed to an immunoglobulin for intravenous administration having reduced complement fixation made by treating an immuno globulin fraction with a low concentration of a sulfitolytic agent and/or phosphate which is sparingly soluble in water. The pH of the material is 7.0, and the product contains 0.85% sodium chloride and 2.5% (g/v) glycine prior to lyophilization.

Teijin Institute of Tokyo is the assignee of record of U.S. Pat. No. 4,059,571 for a novel immunoglobulin derivative. A water soluble composition for intravenous injection which contains the novel derivative is described. The derivative is the S-sulfonated product of cleaved interchain disulfide bonds of gamma globulin.

GLOVENIN, a pepsin-treated human immunoglobulin, is manufactured by Nihon Seigaku of Japan. Typically, a solution of the above product contains 50 mg/ml of pepsin-treated immunoglobulin, 2.25% (w/v) of aminoacetic acid, and 0.85% (w/v) sodium chloride.

Yamanouch Seiyaku is the distributor of GLOBULIN V, a dried pepsin-treated human immunoglobulin (500 mg) containing 225 mg of aminoacetic acid and 85 mg of sodium chloride. For intravenous administration the dried product is disolved in 10 ml of water for injection.

SUMMARY OF THE INVENTION

I have discovered an ummodified intravenously injectable immune serum globulin having an ionic strength and a pH such that the monomer content of the immune serum globulin is greater than about 90% and the actual and latent anticomplement activity is maintained such that the immune serum globulin is intravenously administrable to a broad spectrum of patients.

The product of my invention is prepared by a method wherein an immune serum globulin (ISG) is solubilized to yield a solution of a certain protein concentration. The pH of this solution is adjusted, and the ionic strength of the solution is reduced, to a level such that the monomer content of the ISG is greater than about 90% and the actual and latent anticomplement activity is such that the ISG product is rendered intravenously injectable. The pH and ionic strength are maintained at the above levels during protein concentration adjustment, sterilization, filling into final containers, and the like.

One advantage of the ISG of the invention is that it is intravenously injectable thus avoiding the problems associated with intramuscularly injected material. Furthermore, the present product is substantially free from chemical modification such as occurs in reduction-alkylation, beta-propiolactone treatment, and the like.

An important feature of the product of the invention is that it is substantially free of actual and latent anticomplement activity and also substantially free of polymeric material or "aggregates". Particularly, the product of the invention exhibits enhanced stability over prior art preparations. The material may be kept at room temperature for long periods in the absence of additives with retention of its monomer content and lack of actual and latent anticomplement activity.

Another advantage of the invention is that the intravenously injectable ISG is virtually unchanged in physical measurements and biological functions. Thus, the antibody titers in the present material are not significantly different from the starting material.

DESCRIPTION OF THE PREFERRED EMBODIMENTS

The starting material for the process of this invention is unmodified human immune serum globulin. In the specification and claims the term "immune serum globulin" is used to define the substance also referred to in the literature variously as gamma globulin, IgG and immunoglobulin G. It consists predominantly and preferably of at least about 85 percent of the 7S species of gamma globulin, which has a molecular weight of about 160,000. Any remainder is preferably 9S species, with a molecular weight of about 300,000. Both standard immune and hyperimmune serum globulins, e.g., tetanus, rabies and hepatitis immune serum globulins, can be employed, the modified product being immune and hyperimmune ISG, respectively. Thus, a suitable starting material for the process of this invention is Cohn's Fraction II or Fraction III filtrate. See Cohn et al., *J. Am. Chem. Soc.* 68, 459 (1946); Oncley et al., ibid., 71, 541 (1949).

Fraction II, by ultracentrifugation studies, is predominantly (about 85 percent) the 7S (sedimentation constant of 7) species of gamma globulin with an average molecular weight of 160,000. The remaining protein is essentially 9S material with a M.W. of about 300,000. Wet Fraction II paste (approximately 30 percent solids) is commonly lyophilized to obtain dry ISG powder which is then dissolved and prepared for intramuscular injection as a 16.5 percent sterile solution. Either the wet Fraction II paste or the dry ISG powder is a suitable starting material for the process of this invention.

Gamma globulin obtained by any process which has essentially the same composition of protein components as found in the Cohn Fraction II or Fraction III filtrate can be used as starting material in the present process.

Both standard immune serum globulin and hyperimmune serum globulin can be employed as starting materials. As is well known, the latter is produced from plasma or serum obtained from selected donors who have much higher titers for a specific antibody than is normally found in the average population. These donors have either been recently immunized with a particular vaccine or else they have recently recovered from an infection or disease. These high titer sera or plasmas are pooled and subjected to the usual Cohn fractionation procedures up to the point of isolating Fraction II. The Bureau of Biologics (BoB) antibody standards for hyperimmune serum globulins presently are based on products to be given intramuscularly. These standards are based on the assumption a standard intramuscular dose of the reconstituted globulin (1–10 ml) will be administered. Because the amount of antibody required to achieve a desired immunological response is substantially less when administered intravenously, it will be apparent the I.V. dose will be substantially less than the I.M. dose which will produce the same serum antibody titer. Thus, the dose of intramuscular ISG and hyperimmune serum globulin must be higher than that required to achieve the same serum antibody titer when globulin of the same antibody activity is administered intravenously.

The starting wet paste or lyophilized powder is dissolved in a volume of water or other physiologically-acceptable carrier to provide a protein solution of a concentration of about 0.5–20% preferably about 5 percent. If Fraction III filtrate is employed, the aqueous solution must be concentrated by conventional techniques to the desired protein concentration. Any protein concentration may be used in this method; however, the above-recited range is preferred from a practical standpoint.

After the protein has been dissolved or concentrated, the solution is adjusted to a pH of about 3.5 to 5.0 preferably about 3.8 to 4.2, by addition of a physiologically-acceptable acid such as hydrochloric acid. In general, the pH is adjusted to a point whereat the monomeric material in the protein solution is maintained at a maximum. However, the pH must not be so low as to result in gelation. The temperature should not be harmful to the ISG material. Good results are obtained within the temperature range of about 0°–20° C. It is not necessary to hold the so-adjusted material for any period of time prior to the next step; however, the material may be held, if desired, without detrimental effects.

Following pH adjustment the protein solution is treated to reduce its ionic strength to a level at which the monomer content of the ISG preparation is greater than about 90%, preferably greater than about 95%, and more preferably greater than about 98%, and the actual and latent anticomplement activity is such that the ISG preparation is intravenously injectable. For this purpose the actual anticomplement activity should be greater than about 2 mg protein/C'H50 unit. The nonspecific complement binding capacity of the product is determined using optionally titered complement and hemolysin. The complement binding capacity, known as anticomplement activity, is reported as mg protein product capable of inactivating (binding) one C'H50 unit. One C'H50 unit is defined as the amount of protein capable of inactivating 50% of complement in an optionally titered complement and hemolysin system.

The ionic strength ($\Gamma/2$) of the solution should be such that the product as a 5% protein solution has a nephelometric reading less than about 15 NTU (National Turbidity Units), preferably less than about 2 NTU. The ionic strength ($\Gamma/2$) is defined as follows:

$$\Gamma/2 = \frac{\Sigma \{[C^+]^2 (Z^+)^2 + [C^-]^2 (Z^-)^2\}}{2}$$

where
- $C^+$ = cations including metal ions such as $Na^+$, $K^+$, $Ca^{+2}$, $Mg^{+2}$, and the like,
- $C^-$ = anions including halide ions such as $C^-$, $Br^-$, carboxylic acid salt ions such as acetate or citrate ions, and the like,
- $Z^+$ = the charge of $C^+$, and
- $Z^-$ = the charge of $C^-$.

Preferably, the ionic strength, as defined, is less than about 0.001. The above treatment may be effected by standard procedures such as ultrafiltration, diafiltration, dialysis, etc., or combinations thereof. For example, the protein solution at the appropriate pH may be diafiltered with at least five volume exchanges of water, usually about 4–8 volume exchanges, to reduce the ionic strength to at least about 0.001. During this treatment the concentration of peptides and other impurities such as alcohol are also reduced, generally to trace amounts.

After or during the above treatment, the pH is measured and maintained within the range of about 3.5–5.0.

The protein concentration of the so-treated material is next adjusted to the level desired in the final product, such as, for example, 5%, 10%, 15%, and so forth. This adjustment is accomplished by conventional techniques not detrimental to ISG, e.g., ultrafiltration, reverse osmosis, sublimation, evaporation, etc. Again, the pH of the preparation is maintained within the range of about 3.5–5.0, preferably about 3.8–4.2.

Next, the ISG preparation is treated to render it tonic, i.e., to render it compatible with physiological conditions or render it physiologically acceptable upon injection. In this respect it is important to note that tonicity must be obtained without raising the ionic strength (as defined above) of the preparation. This end is achieved by adding to the ISG preparation an amount of an amino acid, such as glycine and the like, or a carbohydrate, such as maltose, dextrose, fructose, and the like, or a sugar alcohol such as mannitol, sorbitol, etc., or mixtures thereof sufficient to achieve tonicity. Thus, for example the ISG preparation may be mixed with about 10% maltose (on a weight to volume basis) to render the preparation tonic.

After the above adjustment the product is sterilized, usually by sterile filtration through appropriate media, and then filled into final containers. It is also possible to lyophilize the sterile ISG product after filling into final containers. For I.V. use the lyophilized material is dissolved in medically-acceptable water prior to injection. If the product has not been made tonic prior to lyophilization, the lyophilized material must be dissolved in a diluent containing medically-acceptable water and one of the aforementioned substances in an amount to render the preparation tonic.

The ISG of this invention is primarily intended for intravenous administration although the ISG preparation may also be administered intramuscularly if it contains the appropriate excipients. The composition aspect of this invention therefore relates to pharmaceutical compositions comprising a solution, in a pharmaceutically acceptable aqueous carrier adapted for intravenous administration, of an intravenously injectable ISG of this invention. The ISG is substantially pure. The ISG is present in these solutions in any concentration, either suitable for immediate I.V. administration or after dilution, e.g., with water or diluent as mentioned above, to acceptable levels, e.g., about 1-18 percent solution, preferably about 1-15 percent and more preferably about 10 percent for immediate administration, and about 16 percent for dilution prior to administration. The ISG can be administered intravenously alone or in combination with or in conjunction with other blood products, e.g., whole blood, plasma, Plasma Protein Fraction, fibrinogen, clotting factors such as Factor VIII, Factor IX concentrate, and so forth, and albumin.

In its method of use aspect, this invention relates to the intravenous administration, usually to humans, of a pharmaceutical composition as defined above. The composition is administered in a conventional manner, e.g., in an amount which provides adequate therapeutic amounts of antibody. For a 16.5 percent protein solution, about 1-25 ml is the customary single dose. Administration of subsequent dosages is usually within 1-3 weeks, depending upon the severity of the illness and the time of exposure thereto.

As mentioned above the products of the invention may be incorporated into pharmaceutical preparations, which may be used for therapeutic purposes. However, the term "pharmaceutical preparation" is intended in a broader sense herein to include preparations containing a composition in accordance with this invention used not only for therapeutic purposes, but also for diagnostic and reagent purposes as known in the art; for tissue culture wherein organisms such as viruses for the production of vaccines, interferon, and the like, are grown on plasma or on plasma fractions, e.g., Cohn Effluent II+III, Cohn Fraction IV, Cohn Fraction V, and so forth; etc. The pharmaceutical preparation intended for therapeutic use should contain a therapeutic amount of the present composition, i.e., that amount necessary for preventative or curative health measures. If the pharmaceutical preparation is to be employed as a diagnostic or a reagent, then it should contain diagnostic or reagent amounts of such composition. Similarly, when used in tissue culture or a culture medium the medium should contain an amount of such composition sufficient to obtain the desired growth.

The gamma globulin of this invention is substantially free from anticomplement activity, both immediate and latent.

Antibody titer is not significantly different from the starting unmodified gamma globulin, i.e., it is normal or hyperimmune, e.g., tetanus or rabies hyperimmune globulin, depending on the antibody titer of the starting ISG. The antibody molecules are bivalent, as indicated by their ability to precipitate with antigen.

Another characterizing feature of the ISG of this invention is its absence of proteolytic activity. It is known that some samples of ISG form fragments when stored. Such fragmentation is due to proteolytic digestion by a contaminating enzyme often presumed to be plasmin. Fragmentation is undesirable since it causes a decrease in the amount of active antibody in solution. The process of this invention sharply decreases the proteolytic activity in ISG to undetectable levels or at most to trace levels.

A primary and important characteristic of the present product is its stability. The product may be stored for extended periods of time without significant, if any, change in its antibody activity, monomer content, clarity, lack of anticomplement activity and so forth. For example, sterile, final container material prepared in accordance with this invention has been stored at room temperature on the shelf for greater than 6 months without significant changes in the above-mentioned qualities. This stability is obtained through pH and ionic strength adjustments as described above. The art heretofore has not recognized the relationship between pH and ionic strength on the one hand and intravenous injection on the other. As mentioned above, treatment of gamma globulin at pH 4 is known. However, the so-treated material was then returned to about pH 7 for administration to patients. Furthermore, addition of salts such as sodium chloride was employed to obtain tonicity.

A related benefit of the product of the present invention is its lack of buffer capacity. The present product is surprisingly administrable at pH 3.5-5.0. However, since the ionic strength has been reduced to a very low level, there is very little disruption, if any, of the physiological pH such as that which would occur with the administration of a material essentially buffered at pH 3.5-5.0 by the presence of salts.

EXAMPLES

The invention is demonstrated further by the following illustrative examples.

EXAMPLE 1

The pH of Fraction III filtrate (2100 l.) from the Cohn fractionation scheme (Cohn et al, supra) was adjusted to 4.0 by addition of 1 N HCl. Approximately 40 l. of HCl was added at a rate of less than one liter per minute with thorough mixing. The Fraction III filtrate was then metered into an ultrafiltration system. Ultrafiltration and diafiltration were used to reduce the alcohol concentration as rapidly as possible while holding the product temperature less than 10° C. Cold distilled water was used to maintain a constant volume of approximately 350 liters. Flux rates as high as 20 l. per minute were observed. When all the Fraction III filtrate had been concentrated to about 5% protein and the product alcohol concentration had been reduced to less than 8%, seven volume exchanges were performed using cold distilled water. The product temperature was permitted to drift as high as 20° C. The immune serum globulin solution was then concentrated to 8% protein and drained from the ultrafiltration system; 120 l. of 8% immune serum globulin was recovered in a clear "water-like" state. This material had an ionic strength of 0.001 (as determined by calculation) and a pH of 4.2. An aliquot of this material was made tonic with 10% maltose at 5% protein. This was filled into 250 ml bottles (60) for stability and other testing. Initial high pressure liquid chromatography (HPLC) results indicated a monomer level greater than 99%. This lot passed all typical testing for IGIV (Table 1). Several containers were stored at room temperature and after six months, HPLC results indicate the monomer content was still greater than 99%.

TABLE 1

| HPLC Monomer (99.1%) Dimer (0.9%) Trimer (0) Void (0) | |
| --- | --- |
| Anticomplement Activity | 3 mg protein per C'H50 unit |
| PKA | 11% of reference |
| Buffer Capacity | 16.24 meq./l. |
| Ultra-centrifuge | 6.6S 90.8% |
| | 9.8S 9.2% |
| Nephelometer | 1.5 NTU |

A similar aliquot was made tonic by addition of glycine to a concentration of 0.2 M.

EXAMPLE 2

An aliquot (6 l.) of the 120 l. of 8% immune serum globulin prepared in Example 1 was treated with 1 N HCl to obtain a pH of 4.0 and lyophilized.

Water for injection was added to this material to obtain a 5% protein concentration. The reconstituted material exhibited the following characteristics:

TABLE 2

| HPLC Monomer (98.5%) Dimer (1.5%) Trimer (0) Void (0) | |
| --- | --- |
| Anticomplement Activity | 3 mg protein per C'H50 unit |

What is claimed is:

1. A stable, sterile, intravenously injectable pharmaceutical composition comprising an aqueous solution of a therapeutic amount of an immune serum globulin, said solution having an ionic strength such that the solution at 5% protein concentration has a nephelometric reading less than 15 NTU, a pH of about 3.5–5.0, and a physiologically-acceptable tonicity.

2. The composition of claim 1 which further includes other blood products.

3. The composition of claim 1 which includes a material selected from the group consisting of carbohydrates, sugar alcohols, and amino acids in an amount sufficient to render physiologically-acceptable tonicity to the solution.

4. The composition of claim 3 wherein the carbohydrate is maltose.

5. The composition of claim 3 wherein the amino acid is glycine.

6. A method for treating immune serum globulin which comprises
   (a) forming an aqueous solution of an immune serum globulin,
   (b) adjusting the pH of said solution to about 3.5–5.0 by addition of a physiologically acceptable acid,
   (c) treating the solution to reduce its ionic strength ($\Gamma/2$) while maintaining the pH of said solution at 5% protein concentration has a nephelometric reading less than 15 NTU, and
   (d) adjusting the tonicity of the solution to a physiologically acceptable level by addition of an agent selected from the group consisting of amino acids, carbohydrates, and sugar alcohols.

7. The method of claim 6 wherein the solution in Step a has a protein concentration of about 0.5–20% by weight.

8. The method of claim 6 wherein the pH is adjusted to about 3.8–4.2 in Step b and maintained thereat in Step c.

9. The method of claim 6 wherein the solution is diafiltered in Step c.

10. The method of claim 6 which further includes the step of
    (e) sterilizing the solution.

11. A composition comprising the product of claim 6.

12. The method of claim 6 which further includes the step of lyophilizing the solution of Step c.

13. A composition comprising the product of claim 12.

14. A dry composition comprising immune serum globulin which upon solution in water has a pH of about 3.5–5.0 and an ionic strength ($\Gamma/2$) such that the solution at 5% protein concentration has a nephelometric reading less than about 15 NTU.

* * * * *

UNITED STATES PATENT AND TRADEMARK OFFICE
CERTIFICATE OF CORRECTION

PATENT NO. : 4,396,608
DATED : August 2, 1983
INVENTOR(S) : Robert A. Tenold

It is certified that error appears in the above-identified patent and that said Letters Patent are hereby corrected as shown below:

Column 10, claim 6, lines 21 - 24, correct step (c) to recite as follows:

--(c) treating the solution to reduce its ionic strength ($\Gamma/2$) while maintaining the pH of said solution at about 3.5 - 5.0, to a level such that the solution at 5% protein concentration has a nephelometric reading less than 15 NTU, and--.

Signed and Sealed this

Sixth Day of November 1984

[SEAL]

Attest:

GERALD J. MOSSINGHOFF

*Attesting Officer*  *Commissioner of Patents and Trademarks*